(12) United States Patent
Fischell et al.

(10) Patent No.: US 8,114,149 B2
(45) Date of Patent: Feb. 14, 2012

(54) HYBRID STENT WITH HELICAL CONNECTORS

(75) Inventors: David R. Fischell, Fair Haven, NJ (US); Robert E. Fischell, Dayton, MD (US); Rajesh Kalavalapally, Ocean, NJ (US); William A. Easterbrook, III, Westwood, NJ (US)

(73) Assignee: Svelte Medical Systems, Inc., New Providence, NJ (US)

( * ) Notice: Subject to any disclaimer, the term of this patent is extended or adjusted under 35 U.S.C. 154(b) by 0 days.

(21) Appl. No.: 12/582,251

(22) Filed: Oct. 20, 2009

(65) Prior Publication Data

US 2011/0093059 A1     Apr. 21, 2011

(51) Int. Cl.
*A61F 2/06* (2006.01)

(52) U.S. Cl. ........................................................ 623/1.15

(58) Field of Classification Search ................. 623/1.15, 623/1.16, 1.39–1.54, 1.11, 1.13, 1.18–1.23
See application file for complete search history.

(56) References Cited

U.S. PATENT DOCUMENTS

| 5,102,417 | A | | 4/1992 | Palmaz | |
|---|---|---|---|---|---|
| 5,725,572 | A | * | 3/1998 | Lam et al. | 623/1.16 |
| 5,776,161 | A | * | 7/1998 | Globerman | 606/194 |
| 5,807,404 | A | * | 9/1998 | Richter | 623/1.16 |
| 5,827,321 | A | * | 10/1998 | Roubin et al. | 623/1.16 |
| 5,843,164 | A | * | 12/1998 | Frantzen et al. | 623/1.16 |
| 5,964,798 | A | * | 10/1999 | Imran | 623/1.12 |
| 6,033,433 | A | * | 3/2000 | Ehr et al. | 623/1.16 |
| 6,036,725 | A | * | 3/2000 | Avellanet | 623/1.13 |
| 6,056,776 | A | * | 5/2000 | Lau et al. | 623/1.16 |
| 6,066,169 | A | * | 5/2000 | McGuinness | 623/1.16 |
| 6,190,403 | B1 | * | 2/2001 | Fischell et al. | 623/1.16 |
| 6,203,569 | B1 | * | 3/2001 | Wijay | 623/1.15 |
| 6,217,608 | B1 | * | 4/2001 | Penn et al. | 623/1.16 |
| 6,264,687 | B1 | * | 7/2001 | Tomonto | 623/1.16 |
| 6,334,870 | B1 | * | 1/2002 | Ehr et al. | 623/1.16 |
| 6,348,065 | B1 | * | 2/2002 | Brown et al. | 623/1.16 |
| 6,409,754 | B1 | * | 6/2002 | Smith et al. | 623/1.16 |
| 6,416,539 | B1 | * | 7/2002 | Hassdenteufel | 623/1.15 |
| 6,416,543 | B1 | * | 7/2002 | Hilaire et al. | 623/1.16 |
| 6,432,133 | B1 | * | 8/2002 | Lau et al. | 623/1.15 |
| 6,451,049 | B2 | * | 9/2002 | Vallana et al. | 623/1.15 |
| 6,511,505 | B2 | * | 1/2003 | Cox et al. | 623/1.16 |
| 6,530,950 | B1 | * | 3/2003 | Alvarado et al. | 623/1.13 |
| 6,562,067 | B2 | * | 5/2003 | Mathis | 623/1.16 |
| 6,589,276 | B2 | * | 7/2003 | Pinchasik et al. | 623/1.16 |
| 6,616,689 | B1 | * | 9/2003 | Ainsworth et al. | 623/1.16 |
| 6,626,935 | B1 | * | 9/2003 | Ainsworth et al. | 623/1.15 |
| 6,676,697 | B1 | * | 1/2004 | Richter | 623/1.16 |
| 6,730,116 | B1 | * | 5/2004 | Wolinsky et al. | 623/1.16 |

(Continued)

*Primary Examiner* — Alvin J Stewart

(74) *Attorney, Agent, or Firm* — Rosenberg, Klein & Lee

(57) ABSTRACT

The present invention is a hybrid stent design using half-slot circumferential sets of strut members with short (<1.5 mm) slot length that has minimal fish scaling and excellent stent retention and flexibility. These half-slot circumferential sets of strut members are connected one to the other with helical connectors similar to those of the Palmaz stent. One important difference in the design of the stent of the present invention is that the helical connectors are attached to every other crown (rather than connected to every crown) to further improve stent flexibility. By appropriately varying the strut width of both the connected and unconnected curved crowns to be greater at the center than at their ends, an increased radial strength can be provided for a given maximum strain that is imparted to the stent when it is expanded to its maximum diameter.

21 Claims, 7 Drawing Sheets

U.S. PATENT DOCUMENTS

| | | | |
|---|---|---|---|
| 6,746,479 B2 * | 6/2004 | Ehr et al. | 623/1.16 |
| 6,764,507 B2 * | 7/2004 | Shanley et al. | 623/1.16 |
| 6,896,697 B1 * | 5/2005 | Yip et al. | 623/1.15 |
| 6,899,729 B1 * | 5/2005 | Cox et al. | 623/1.13 |
| 6,916,336 B2 * | 7/2005 | Patel et al. | 623/1.16 |
| 6,981,986 B1 * | 1/2006 | Brown et al. | 623/1.16 |
| 7,044,963 B1 * | 5/2006 | Richter | 623/1.15 |
| 7,131,993 B2 * | 11/2006 | Gregorich | 623/1.16 |
| 7,195,648 B2 * | 3/2007 | Jones et al. | 623/1.16 |
| 7,264,633 B2 * | 9/2007 | Bonsignore | 623/1.15 |
| 7,431,732 B2 * | 10/2008 | Moriuchi et al. | 623/1.15 |
| 7,534,257 B2 * | 5/2009 | Richter | 623/1.15 |
| 7,556,644 B2 | 7/2009 | Burpee et al. | |
| 7,789,905 B2 * | 9/2010 | Von Oepen et al. | 623/1.15 |
| 7,803,180 B2 * | 9/2010 | Burpee et al. | 623/1.15 |
| 7,862,607 B2 * | 1/2011 | McDermott et al. | 623/1.16 |
| 7,862,608 B2 * | 1/2011 | Hogendijk et al. | 623/1.22 |
| 7,867,272 B2 * | 1/2011 | Niermann | 623/1.15 |
| 7,875,068 B2 * | 1/2011 | Mangiardi et al. | 623/1.15 |
| 2001/0044653 A1 * | 11/2001 | Kveen et al. | 623/1.16 |
| 2002/0007212 A1 * | 1/2002 | Brown et al. | 623/1.16 |
| 2002/0032478 A1 * | 3/2002 | Boekstegers et al. | 623/1.16 |
| 2002/0045935 A1 * | 4/2002 | Jang | 623/1.16 |
| 2002/0049493 A1 * | 4/2002 | Jang | 623/1.16 |
| 2002/0123796 A1 * | 9/2002 | Majercak et al. | 623/1.16 |
| 2002/0123797 A1 * | 9/2002 | Majercak | 623/1.16 |
| 2002/0123799 A1 * | 9/2002 | Burgermeister | 623/1.17 |
| 2002/0156525 A1 * | 10/2002 | Smith et al. | 623/1.22 |
| 2002/0161430 A1 * | 10/2002 | Jang | 623/1.16 |
| 2002/0177893 A1 * | 11/2002 | Brown et al. | 623/1.16 |
| 2003/0149469 A1 * | 8/2003 | Wolinsky et al. | 623/1.11 |
| 2003/0158596 A1 * | 8/2003 | Ikeuchi et al. | 623/1.16 |
| 2004/0054400 A1 * | 3/2004 | Granada | 623/1.16 |
| 2004/0088044 A1 * | 5/2004 | Brown et al. | 623/1.16 |
| 2004/0230296 A1 * | 11/2004 | Brown et al. | 623/1.16 |
| 2004/0267353 A1 * | 12/2004 | Gregorich | 623/1.16 |
| 2005/0131530 A1 * | 6/2005 | Darack | 623/1.16 |
| 2006/0020325 A1 * | 1/2006 | Burgermeister et al. | 623/1.16 |
| 2006/0064158 A1 * | 3/2006 | Bales et al. | 623/1.22 |
| 2006/0136040 A1 * | 6/2006 | Burgermeister et al. | 623/1.16 |
| 2006/0224234 A1 * | 10/2006 | Jayaraman | 623/1.16 |
| 2007/0010872 A1 * | 1/2007 | Gregorich | 623/1.16 |
| 2007/0038289 A1 * | 2/2007 | Nishide et al. | 623/1.16 |
| 2007/0050011 A1 * | 3/2007 | Klein et al. | 623/1.16 |
| 2007/0067017 A1 * | 3/2007 | Trapp | 623/1.16 |
| 2007/0073384 A1 * | 3/2007 | Brown et al. | 623/1.16 |
| 2007/0073385 A1 * | 3/2007 | Schaeffer et al. | 623/1.16 |
| 2007/0100434 A1 * | 5/2007 | Gregorich et al. | 623/1.16 |
| 2007/0123974 A1 * | 5/2007 | Park et al. | 623/1.16 |
| 2007/0150050 A1 * | 6/2007 | Lenz | 623/1.16 |
| 2007/0168015 A1 * | 7/2007 | Momma et al. | 623/1.16 |
| 2007/0208416 A1 * | 9/2007 | Burpee et al. | 623/1.22 |
| 2007/0219626 A1 * | 9/2007 | Rolando et al. | 623/1.16 |
| 2007/0239263 A1 * | 10/2007 | Fliedner | 623/1.16 |
| 2008/0009932 A1 * | 1/2008 | Ta et al. | 623/1.11 |
| 2008/0065196 A1 * | 3/2008 | Davis et al. | 623/1.16 |
| 2008/0065197 A1 * | 3/2008 | Meyer et al. | 623/1.16 |
| 2008/0097579 A1 * | 4/2008 | Shanley et al. | 623/1.16 |
| 2008/0140182 A1 * | 6/2008 | Scheller | 623/1.17 |
| 2008/0167707 A1 * | 7/2008 | Marrey et al. | 623/1.16 |
| 2008/0195192 A1 * | 8/2008 | Parsonage | 623/1.16 |
| 2008/0249608 A1 * | 10/2008 | Dave | 623/1.16 |
| 2008/0281404 A1 * | 11/2008 | Lee et al. | 623/1.16 |
| 2008/0294238 A1 * | 11/2008 | Tischler et al. | 623/1.16 |
| 2009/0036972 A1 * | 2/2009 | Gale et al. | 623/1.16 |
| 2009/0069881 A1 * | 3/2009 | Chalekian et al. | 623/1.16 |
| 2009/0069882 A1 * | 3/2009 | Venturelli et al. | 623/1.16 |
| 2009/0076591 A1 * | 3/2009 | Girton et al. | 623/1.16 |
| 2009/0149943 A1 * | 6/2009 | Tower | 623/1.16 |
| 2009/0240318 A1 * | 9/2009 | Chalekian et al. | 623/1.16 |
| 2009/0306766 A1 * | 12/2009 | McDermott et al. | 623/1.16 |
| 2010/0057190 A1 * | 3/2010 | Issenmann | 623/1.16 |
| 2010/0070021 A1 * | 3/2010 | Wack et al. | 623/1.16 |
| 2010/0070022 A1 * | 3/2010 | Kuehling | 623/1.16 |
| 2010/0121430 A1 * | 5/2010 | Kveen et al. | 623/1.16 |
| 2010/0131044 A1 * | 5/2010 | Patel | 623/1.16 |
| 2010/0131045 A1 * | 5/2010 | Globerman et al. | 623/1.16 |
| 2010/0137974 A1 * | 6/2010 | Chouinard et al. | 623/1.16 |
| 2010/0204779 A1 * | 8/2010 | Schuessler et al. | 623/1.16 |
| 2010/0204780 A1 * | 8/2010 | Fliedner et al. | 623/1.16 |
| 2010/0228337 A1 * | 9/2010 | Milisav | 623/1.16 |
| 2010/0233229 A1 * | 9/2010 | Nakagawa et al. | 424/422 |
| 2010/0234936 A1 * | 9/2010 | Schlun | 623/1.16 |
| 2010/0241215 A1 * | 9/2010 | Hansen et al. | 623/1.16 |
| 2010/0241217 A1 * | 9/2010 | Kveen et al. | 623/1.16 |
| 2010/0274348 A1 * | 10/2010 | Schaffner et al. | 623/1.16 |
| 2011/0004290 A1 * | 1/2011 | Bales et al. | 623/1.16 |

* cited by examiner

HYBRID STENT WITH HELICAL CONNECTORS

FIELD OF USE

This invention is in the field of stents for implantation into a vessel of a human body.

BACKGROUND OF THE INVENTION

Stents are well known medical devices that have been used for maintaining the patency of a large variety of vessels of the human body. The most frequent use for stents is for implantation into the coronary vasculature. Although stents have been used for this purpose for more than twenty years, many stent designs still lack the required flexibility and radial rigidity to provide an optimum clinical result and also have fractures after many years of exposure to the flexing of a coronary artery.

Most current tubular stents use a multiplicity of circumferential sets of strut members connected by either straight longitudinal connecting links or undulating longitudinal connecting links. The circumferential sets of strut members are typically formed by connecting relatively straight segments with straight struts as the end crown (as with the Palmaz stent sold by Cordis a Johnson & Johnson Company) or with curved crowns (as with the BX Velocity stent, described in U.S. Pat. No. 6,190,403 by Fischell et al, sold by Cordis a Johnson & Johnson Company). In any case, each circumferential set of strut members forms a closed cylindrical ring that opens up as the stent expands and forms the cylindrical structure that acts as a scaffold which supports the dilated arterial wall. There are two basic forms of circumferential sets of strut members: full-slot circumferential sets of strut members having structures where the circumferential set of strut members open radial outward from a series of rectangles to form diamond like structures (the Palmaz stent) and half-slot circumferential sets of strut members which resemble more of a sine wave circumferential ring (such as the BX Velocity stent). The longitudinal dimension of the opening inside each circumferential set of strut members of the unexpanded stent is called the slot length.

In FIGS. 7-10 of U.S. Pat. No. 5,102,417, (the '417 patent) the Palmaz spiral stent design is shown that has full-slot circumferential sets of strut members with every straight end, square crown connected by a helical connector to a crown of the adjacent full-slot circumferential set of strut members. This design typically has only three full-slot circumferential sets of strut members for a stent that is 15 mm long. This full-slot design creates a long, straight, rigid, longitudinal structure with slot length typically greater than 4 mm in the unexpanded stent. This long slot length limits the stent's flexibility and therefore limits the stent's ability to be advanced through a curved coronary artery. Another disadvantage of the long slot design of Palmaz is that the long and rigid circumferential sets of strut members cause the ends of the circumferential sets of strut members to separate from the balloon and engage the arterial wall when the stent is advanced through a curved coronary artery. This phenomenon is known as "fish scaling" because the ends of the long strut members stick out from the surface of a curved balloon like the scale of a fish. Fish scaling can cause stent embolization or it can prevent the stent from being advanced through a highly curved coronary artery. The long, longitudinally straight structure of the Palmaz stent having the full-slot circumferential sets of strut members also have a tendency to easily slide off the delivery balloon thereby increasing the probability of stent embolization. In addition, with every crown of each full-slot circumferential set of strut members connected to the adjacent circumferential set of strut members, the ability of the stent to bend around a curve is limited. It is the lack of flexibility that prevented the stent described in the '417 patent from becoming a great commercial success. For the purposes of this disclosure, stents like that shown in FIGS. 7-10 of '417 patent, with each end crown of a circumferential set of strut members connected to a crown of an adjacent circumferential set of strut members is called a fully connected or closed cell stent. A stent with less than half of the crowns connected is generally called an open cell stent and a stent with every other crown connected is called a hybrid stent. It should also be noted that stent design of the '417 patent has struts that have a uniform width even though having a variable strut width can offer performance advantages as to maximizing the stent's radial rigidity while limiting maximum strain to a level below that that can cause fracture and fatigue failure.

SUMMARY OF THE INVENTION

The present invention is a hybrid stent design using half-slot circumferential sets of strut members with short (<1.5 mm) slot length that has minimal fish scaling and excellent stent retention and flexibility. These half-slot circumferential sets of strut members are connected one to the other with helical connectors similar to those of the Palmaz stent. One important difference in the design of the stent of the present invention is that the helical connectors are attached to every other crown (rather than connected to every crown) to further improve stent flexibility. Another important difference is that the stent design of the present invention utilizes curved crowns having a variable strut width. By appropriately varying the strut width of the curved crowns to be greater at the center than at the ends, an increased radial strength can be provided for a given maximum strain that is imparted to the stent when it is expanded to its maximum diameter.

When the center of each curved crown is directly opposed to the valley in the adjacent circumferential set of strut members, it is called an "in-phase" design of the circumferential set of strut members. This is in contradistinction to the stent design described in the '417 patent where each crown is directly opposed to a crown of the adjacent circumferential set of strut members which is called an "out-of-phase" design. The present invention could have circumferential sets of strut members that can be either in-phase or out-of-phase depending upon the arc length of the helical connector that is selected. With either the out-of-phase or in-phase designs, the helical connectors can have different arc lengths with even number of cycles for the out-of-phase designs and a multiplicity of half-cycles for the in-phase designs.

As the connectors in stents act as the hinge point for a stent to bend as it is advanced around a bent, the hybrid type stent design with every other crown connected provides much greater flexibility for the stent as compared to a closed cell design with every crown connected. This is because there are half as many connectors that join the circumferential set of strut members which significantly reduces the stent's stiffness.

An important advantage of an in-phase design with 1.5 cycle offsets for the helical connectors is that each helical connector has a greater length as compared to the length of a single cycle offset helical connector shown in the '417 patent. Because a longer helical connector provides additional flexibility, for implantation into highly curved coronary arteries, use of the in-phase design with elongated helical connectors offers a significant advantage. A feature of the stent that also provides improved flexibility, eliminates fish scaling and provides better stent retention onto the balloon is that the longitudinal length of each circumferential set of strut members is less than half (<1.5 mm) as great as the 4 mm slot length of the circumferential sets of strut members as taught in the '417 patent. The novel combination of short, half slot, strut members with every other crown being connected with either a one or 1.5 cycle long helical connector will result in significantly improved stent flexibility as compared to the Palmaz stent design described in the '417 patent.

Another important feature of the present invention is that each curved crown of each circumferential set of strut members is shaped so that the maximum material strain when the stent is expanded to its maximum rated diameter will be the approximately the same for connected crowns that attach to a helical connector and unconnected crowns that do not. Still further, maximizing the radial stiffness of the stent while maintaining a maximum material strain that is below the safety limit where fractures or fatigue failure can occur can be achieved by adjusting the shape of the interior curve of each crown that is connected to a straight connector to be different from the shape of the interior curve of those crowns that are not connected. This is necessary to achieve the goal of each interior curved surface of each crown being designed to have approximately the same maximum strain that is just below the safety limit for the metal of the stent when the stent is expanded to its maximum rated diameter. Another advantage for each crown having approximately the same strain during expansion is that the circumferential sets of strut members will open uniformly.

While in-phase and out-of-phase designs have been described, the present invention concepts are also applicable to stents that are between in-phase and out-of phase designs.

To clearly describe the stent design of the present invention, it is important to define the direction of rotation that the helical connectors have as they are connected to crowns of adjacent circumferential sets of strut members. If one views a cylindrical stent drawing from its left side, the helical connectors can have a rotation that is either clockwise or counter clockwise. In the flat, layout view of the stent, if a helical connector has its left side connector lower than its right side connection to a crown, then this helical connector is said to have a positive slope which corresponds to a counter clockwise rotation of the cylindrical stent. If the flat, layout view of the stent has the connectors being connected to a crown on its left to be higher than its connection to the adjacent crown on its right, then that corresponds to a clockwise rotation of the helical connector of the cylindrical stent, which in the flat, layout view of the stent is said to be a negative slope.

The helical connectors of the '417 patent are all in the same counter clockwise direction; i.e.; they have a positive slope when shown in the flat, layout view of the stent. Having all the stent connectors in the same direction can induce a twist into the stent that has been shown in experiments to increase foreshortening of the stent during expansion. This is most evident in longer stents that have many connectors. By alternating the slope or rotation of the connectors on either side of each circumferential element or by having the proximal half of the stent with connectors that rotate in one direction and the distal half rotate in the opposite direction, this stent twisting can be reduced and the stent will have less foreshortening thereby providing better coverage of the entire length of stented vessel. It is also envisioned that within a set of helical connectors that are connected to the same adjacent circumferential sets of strut members, that some helical connectors might extend clockwise while others extend counter clockwise. It should be remembered that clockwise and counter clockwise corresponds respectively to negative or positive slopes on a typical flat, layout drawing of the stent, which layout drawing is typically used for design and manufacturing. The feature of the present invention which has different connectors sloped in opposite directions on different parts of the stent is another novel feature which differentiates the present invention from the prior art.

Another novel aspect of this stent design is that the inside shape of the crowns that are connected are shaped differently from the inside curve of the unconnected crowns so as to allow the maximum strain to be matched between connected and unconnected crowns thereby maximizing stent strength and improving the uniformity of expansion. Still further, another important and novel aspect of the design of this stent is that the helical connectors have a tangential connection to the outer curve of the connected crowns. This tangential connection without any undulation improves the resistance of the stent to axial fatigue failure over many millions of stress cycles as would occur when the stent is implanted in a curved coronary artery.

Thus an object of the present invention is to have an extremely flexible stent having half-slot circumferential sets of strut members with slot length of less than 1.5 mm with helical connectors attached to every other crown and with each circumferential set of strut members being either in-phase or out-of-phase. The object of this design is to improve stent retention, provide great flexibility and to essentially eliminate fish scaling as the stent is advanced through any highly curved coronary artery.

Another object of this invention is to have approximately the same maximum strain of both the connected and unconnected crowns when the stent is expanded to its maximum nominal diameter by having different shapes for the interior curved surface of each of the crowns.

Still another object of this invention is to have helical connectors at different locations on the stent that slope in opposite directions to reduce stent twist during expansion.

Still another object of this invention is to have the arc length of the helical connectors to be less than 90 degrees.

Still another object of the present invention is to have the helical connectors connect tangentially to the outer surface of the connected crowns.

These and other objects and advantages of this invention will become obvious to a person of ordinary skill in this art upon reading the detailed description of this invention including the associated drawings as presented herein.

DETAILED DESCRIPTION OF THE INVENTION

Figure 1:
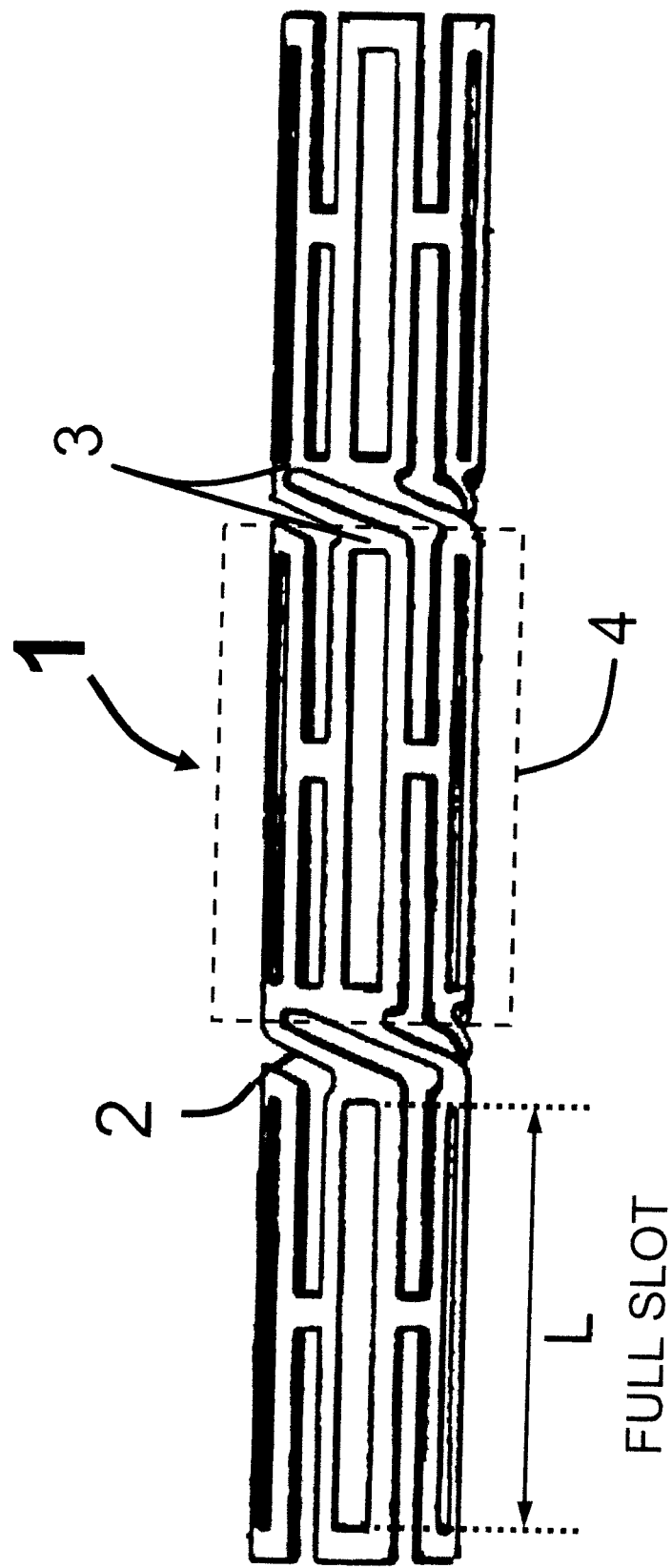
FIG. 1 is a side view of the closed cell, Palmaz stent as presented in FIG. 9 of the '417 patent.

FIG. 1 is a side view of the "PRIOR ART" Palmaz spiral stent 1 which is shown (with different element numbers) in FIG. 9 of U.S. Pat. No. 5,102,417. The stent 1 has full slot circumferential sets of strut members 4. This stent has helical connectors 2 that connect to the interior square-end straight crowns 3 of the stent 1. Thus this design is a closed-cell stent because every interior crown 3 is connected to a crown 3 of an adjacent circumferential set of strut members 4. The stent 1 has helical connectors 2 to connect the square-end or straight crowns 3 of each of the three circumferential sets of strut members 4 to a crown 3 of an adjacent circumferential set of strut members 4. This is also called an out-of-phase design since each adjacent circumferential set of strut members 4 is out-of-phase in the circumferential direction with the adjacent circumferential set of strut members 4. In this stent design, each full slot circumferential sets of strut members has a length "L". The Palmaz spiral stent design (as shown in FIG. 1) which was commercialized in the mid-1990s for use in coronary arteries had only three circumferential sets of strut members 4 each being more than 4 mm long for a stent that had a total length of 15 mm. As described herein, this full-slot design makes for a comparatively inflexible stent that is not easily advanced through highly curved coronary arteries.

Although stents are in fact cylindrical tubes (as shown in the side view of FIG. 1), they are often illustrated in the form of a flat, two-dimensional layout view as shown in FIGS. 2 to 7 inclusive. The flat layout view is actually superior to a side view of the cylindrical stent because it better illustrates the details of how the stent is designed. Modern stents are also designed using flat layout computer aided designs that can be easily converted to machine instructions for laser cutting the stent using automated laser stent cutting machines.

Figure 2:
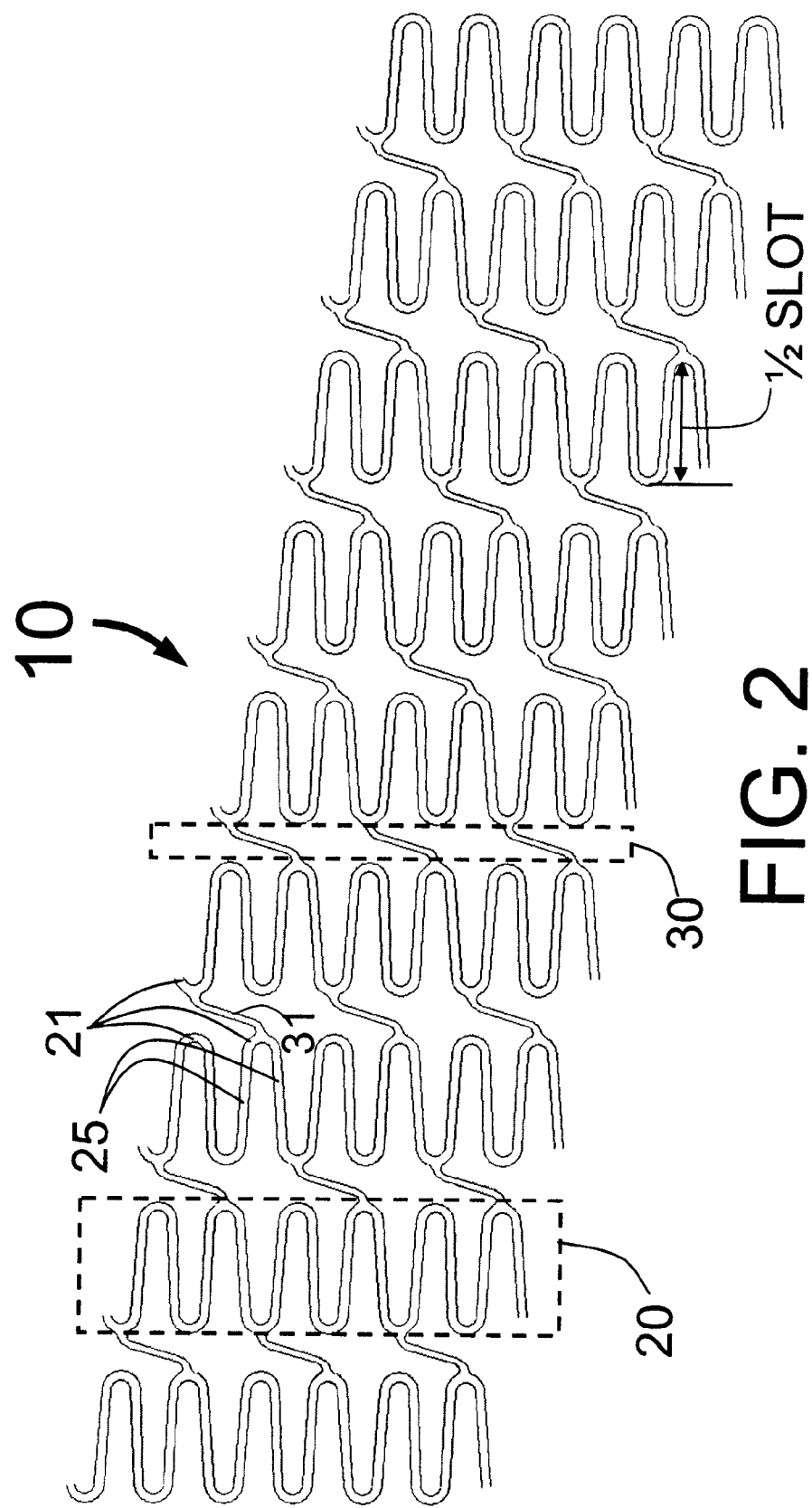
FIG. 2 is a flat layout view of the present invention in the embodiment of a hybrid stent with helical connectors shown as cut before crimping onto a delivery balloon with the out-of-phase arrangement of the circumferential sets of strut members.

FIG. 2 is a flat layout view of the stent 10 shown as cut before crimping onto a delivery balloon. The stent 10 includes a multiplicity of longitudinally spaced, out-of-phase in the circumferential direction; circumferential sets of strut members 20 connected one to the other by a set of helical connectors 30. The fact that every other crown of each circumferential set of strut members is connected to the adjacent circumferential set of strut members indicates that this is a hybrid stent design; i.e., it is neither an open cell design that would have fewer than three connectors nor a closed cell design that would have every crown connected to a crown of an adjacent circumferential set of strut members. Each half-slot circumferential set of strut members 20 includes straight segments 25 connected to curved crowns 21 to form a cylindrical, ring-like structure that can expand radially outward to press against the wall of a blood vessel. Each circumferential set of strut members 20 connects to at least one adjacent circumferential set of strut members 20 by individual helical connectors 31 which attach to every other crown 21. This differs from the prior art Palmaz closed cell design (of FIG. 1) in which every crown attaches to a helical connector. This hybrid design greatly enhances the ability of the stent 10 to be advanced through a curved coronary artery as compared to the design of FIG. 1 because only every other crown is connected to a connector as opposed to the connectors being connected to every crown. Half as many connections between the circumferential sets of strut members significantly increases stent flexibility. In addition, the slot length (marked "½ SLOT" in FIG. 2) of each circumferential set of strut members 20 in the design of the present invention is less than 1.5 mm in length compared to the more than 4 mm length of the full slots of the Palmaz stent of FIG. 1. Ideally, the half-slot length should be between 0.8 and 1.3 mm. Such short slot lengths of the present invention provide much greater flexibility and greatly reduced tendency for fish scaling as compared to the Palmaz stent design of FIG. 1.

Although the design of FIG. 2 shows circumferential sets of strut members 20 with six crowns 21 at each end connected by three helical connectors 31, it is envisioned that such a hybrid stent could have 4, 8, 10, 12 or more crowns 21 around with always half as many helical connectors 31 as crowns 21. It is also envisioned that the stent 10 can be made shorter in its longitudinal length by having fewer circumferential sets of strut members 20 or longer lengths can be made by including more circumferential sets of strut members 20 using the means of connection as shown in FIG. 2.

Figure 3:
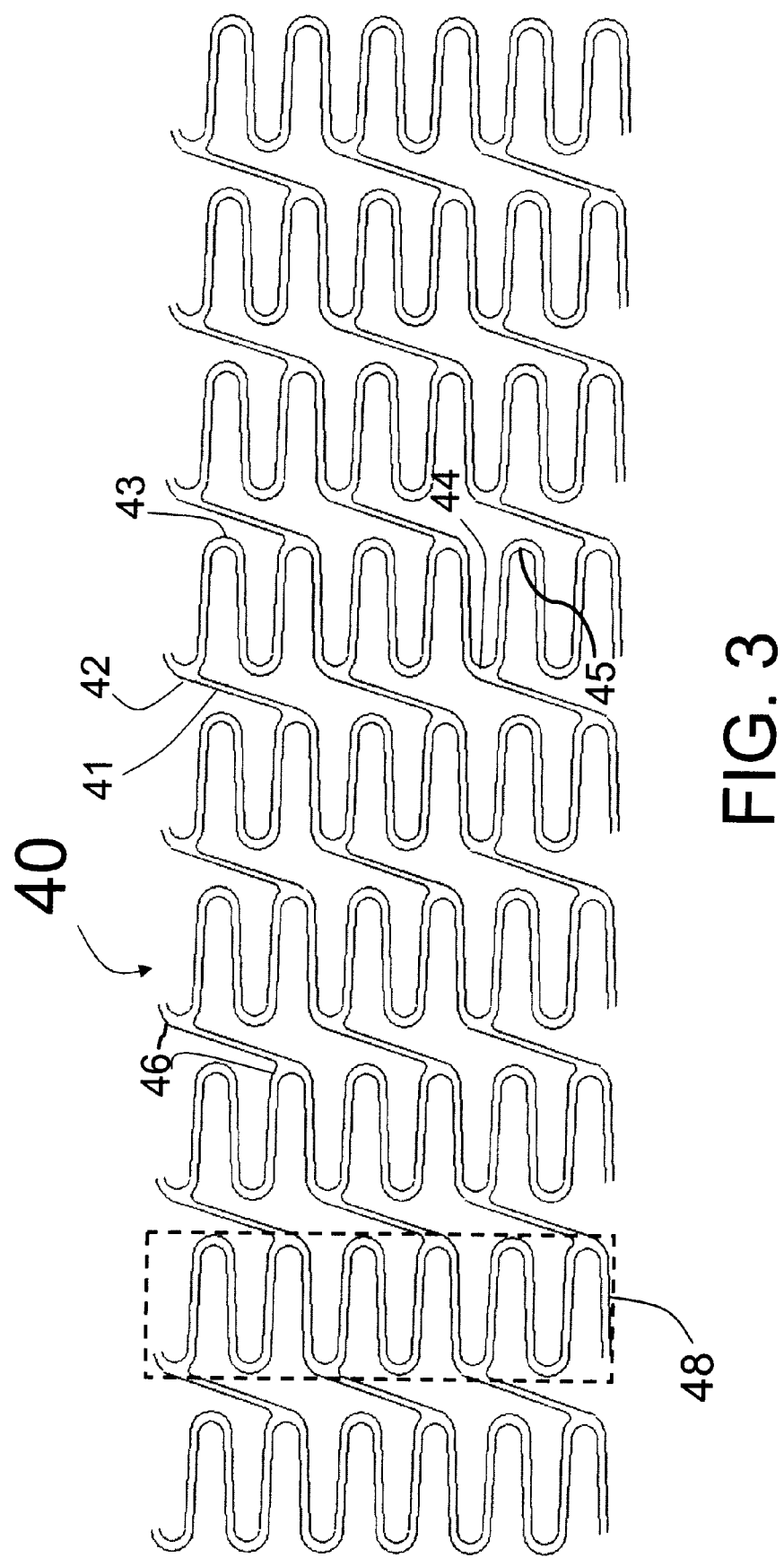
FIG. 3 is a flat layout view of the present invention in the embodiment of a hybrid stent with helical connectors shown as cut before crimping onto a delivery balloon with the in-phase arrangement of the circumferential sets of strut members that provides for an elongated length of the helical connectors.
Figure 4:
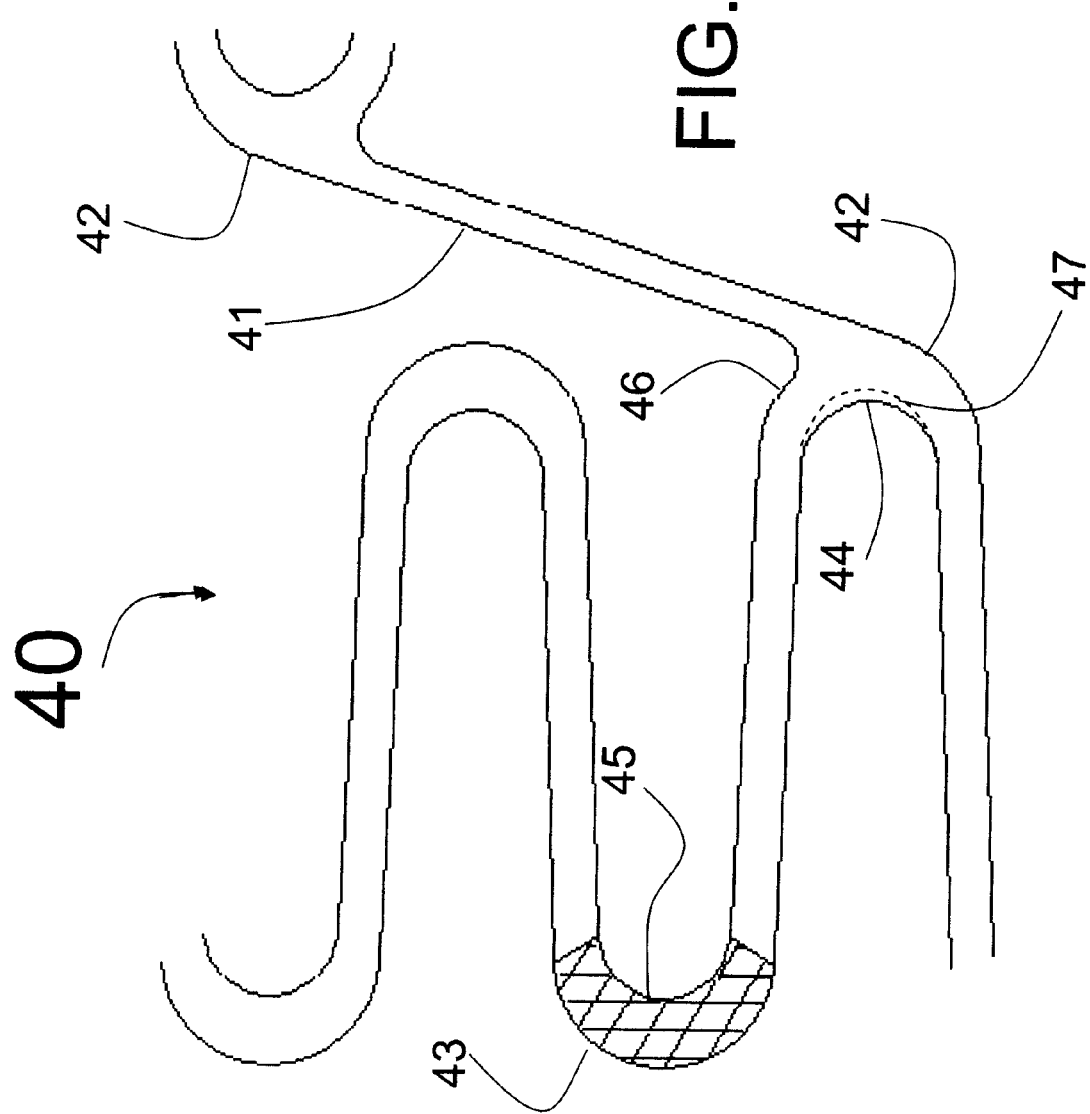
FIG. 4 is an enlarged view of the stent that is shown in FIG. 3 showing details of the connection of the helical connector to the variable width crowns of the circumferential set of strut members and showing both connected and unconnected crowns.

FIGS. 3 and 4 illustrate a stent 40 that is an alternative embodiment of the present invention where there is an in-phase arrangement of the circumferential sets of strut members 48. This design allows for elongated, helical connectors 41 that are longer than the helical connectors 31 of FIG. 2. The longer connectors 31 further improve the flexibility of the stent. FIG. 3 shows a stent 40 having elongated, helical connectors 41 that have a tangential connection 42 to the curved, variable width connected crowns 44. This is in contradistinction to the helical connectors 31 of FIG. 2 that are somewhat curved where they attach to the crowns 21. This tangential connection 42 of the helical connectors 41 improves the resistance of the stent to fatigue failure after millions of cycles of bending that would occur over many years in curved coronary arteries.

The interior curves 44 of the connected crowns 46 and the interior curves 45 of the unconnected crowns 43 are each shaped to provide a variable crown width that can increase the radial rigidity of the stent while limiting the maximum strain of the metal to a level below the safety limit to prevent fracture and fatigue failure when the stent 40 is expanded within a coronary (or peripheral) artery. The difference between the interior curves 44 and 45 is explained with reference to FIG. 4.

FIG. 4 shows an enlarged, layout view of a single elongated, helical connector 41 of the stent 40. For this design, each one of the two, parallel outer edges of the connector 41 is tangential at the connection 42 to the outer curved surface of the connected crown 46. This tangential connection 42 of the helical connector 41 is an improved structural design that resists the bending failures that can occur during fatigue testing for highly curved and therefore weaker connecting structures.

The crosshatched section of the crown 43 of FIG. 4 illustrates the variable strut width of these unconnected crowns 43. A novel feature of the design of the stents of FIGS. 2 to 7 inclusive is that the tapered shapes of the crowns 43 and 46 are different from each other.

The interior curve 45 of the unconnected crowns 43 is adjusted to maximize the radial rigidity of each circumferential set of strut members when the metal reaches its maximum strain as the stent 40 is expanded to its maximum rated diameter. The connected crowns 46 of the stent 40 can have an interior curve 44 or the dotted interior curve 47. The curve 44 has the same radius as the curve 45 but is typically offset in the horizontal direction by a different amount than the curve 45 so that even with the added metal in the crown 46 due to the attachment of the helical connector 41, the crowns 45 and 46 will each reach the same maximum strain level as the stent 40 is expanded to its maximum rated diameter. This improved structure for the stent 40 can also be achieved by using a different shaped interior curve 47 of crown 46 where the shape of the curve 47 is such that the crowns 45 and 46 will each reach the same maximum strain level as the stent 40 is expanded to its maximum rated diameter. The optimum interior curve for the connected crowns 46 could optimally be approximately the shape of the dotted curve 47 as shown in FIG. 4.

To further enhance the flexibility of the stent 40, it is important to have the strut width of the connectors 41 to be significantly thinner than the average strut width of each circumferential set of strut members. Typically, the strut width of the helical connectors 41 should be at least 30% thinner as compared to the average strut width of the unconnected crowns 43. This makes sense as the circumferential sets of strut members 48 provide the radial rigidity of the stent to resist pressure from the artery wall while the connectors 41 need to flex to allow the stent to bend as it is advanced to the treatment site.

It should be understood that the present invention can be practiced somewhat differently as compared to the specific designs shown in FIGS. 2, 3 and 4. Specifically, connectors 31 or 41 can be of a variety of lengths depending upon whether the circumferential sets of strut members are in-phase or out-of-phase and dependent upon how many crowns apart is the spacing for the connection of the straight connectors 31 or 41. For example, in FIG. 2 each helical connector 31 could be lengthened by attachment to a crown 21 that is further away from the other connected crown 31 as shown in FIG. 2. In FIG. 3, the helical connector 41 could be shortened by attachment to the closest connected crown 46 of the adjacent circumferential set of strut members. Thus, a large variety of the lengths of the helical connectors 31 or 41 is possible, each of which will have somewhat different characteristics when the stent 10 or 40 is crimped onto a balloon and when it is expanded to open a stenosed blood vessel.

Figure 5:
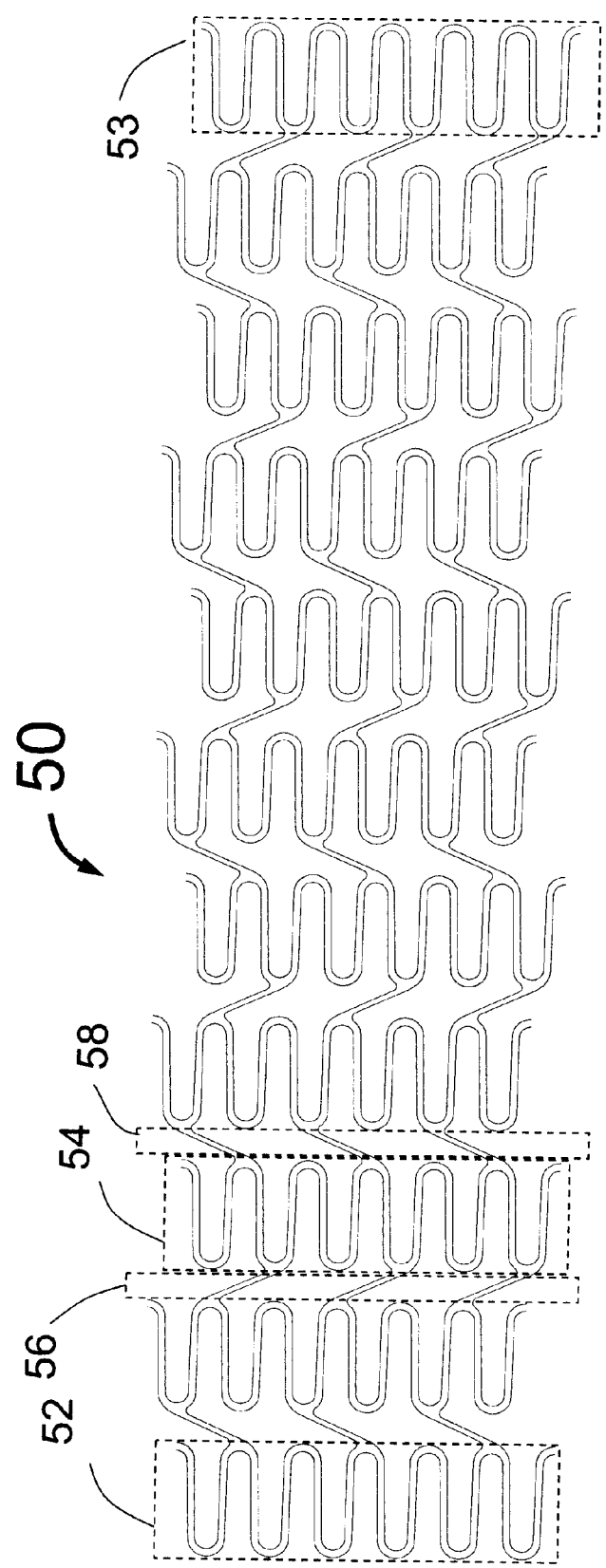
FIG. 5 is flat layout view of the present invention stent with tapered crowns and out-of-phase circumferential sets of strut members with every other set of helical connectors sloping in opposite directions.

FIG. 5 is flat layout view of another embodiment of the present invention stent 50 with a proximal end (left side) circumferential set of strut members 52, a distal end (right side) circumferential set of strut members 53 and one or more central circumferential sets of strut members 54. The sets of helical connectors 56 and 58 that connect on opposite sides of the circumferential set of strut members 54 have different slopes with the set 56 having a negative slope and the set 58 having a positive slope. A positive slope has the top end of the helical connector being to the right of the bottom end and a negative slope of the helical connector has the top end of the connector to the left of the bottom end of the connector. It is advantageous to have helical connector sets 56 and 58 that slope in opposite directions to reduce stent twisting during expansion that can occur for example with the stent 10 of FIG. 2 where all of the helical connectors have a positive slope. The design of FIG. 2 could have a considerable degree of twisting that can cause the stent to foreshorten as it is expanded in a coronary artery. Reduced twisting may also reduce the induced strain in the stent during expansion and can increase the uniformity of expansion. It should be remembered that these negative or positive slopes in a flat, layout drawing of a stent actually correspond respectively to clockwise or counter clockwise rotation of the helical connector in the actual three dimensional stent as one views the stent from its left end.

Figure 6:
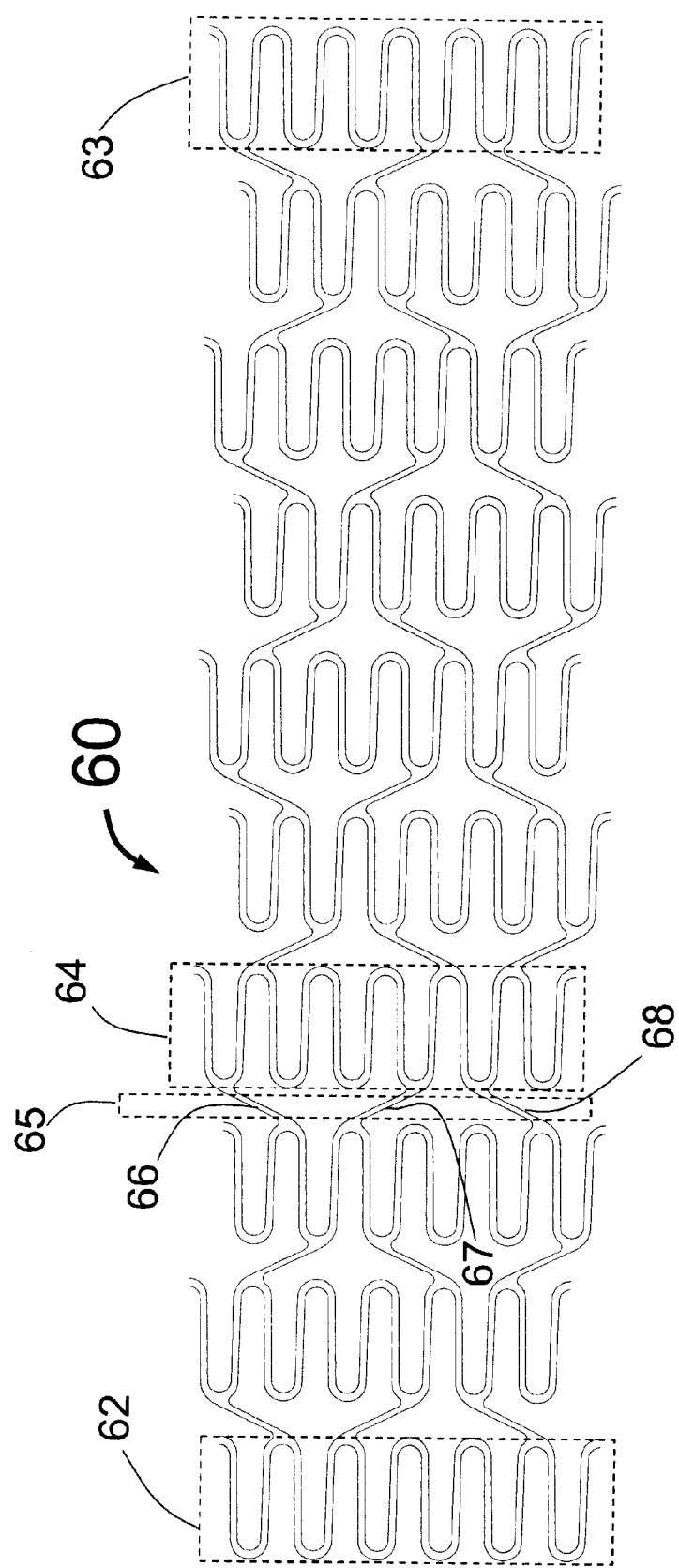
FIG. 6 is flat layout view of the present invention stent with tapered crowns and out-of-phase circumferential sets of strut members where some of the helical connectors within each set of helical connectors slope in opposite directions.

FIG. 6 is flat layout view of still another embodiment of the stent 60 with a proximal end (left side) circumferential set of strut members 62, a distal end (right side) circumferential set of strut members 63 and one or more central circumferential sets of strut members 64. In this embodiment of the present invention, each set of helical connectors 65 includes two connectors that slope in one direction and one connector that slopes in the opposite direction. Specifically, in the set 65 the helical connectors 66 and 68 have a positive slope and the helical connector 67 has a negative slope.

Figure 7:
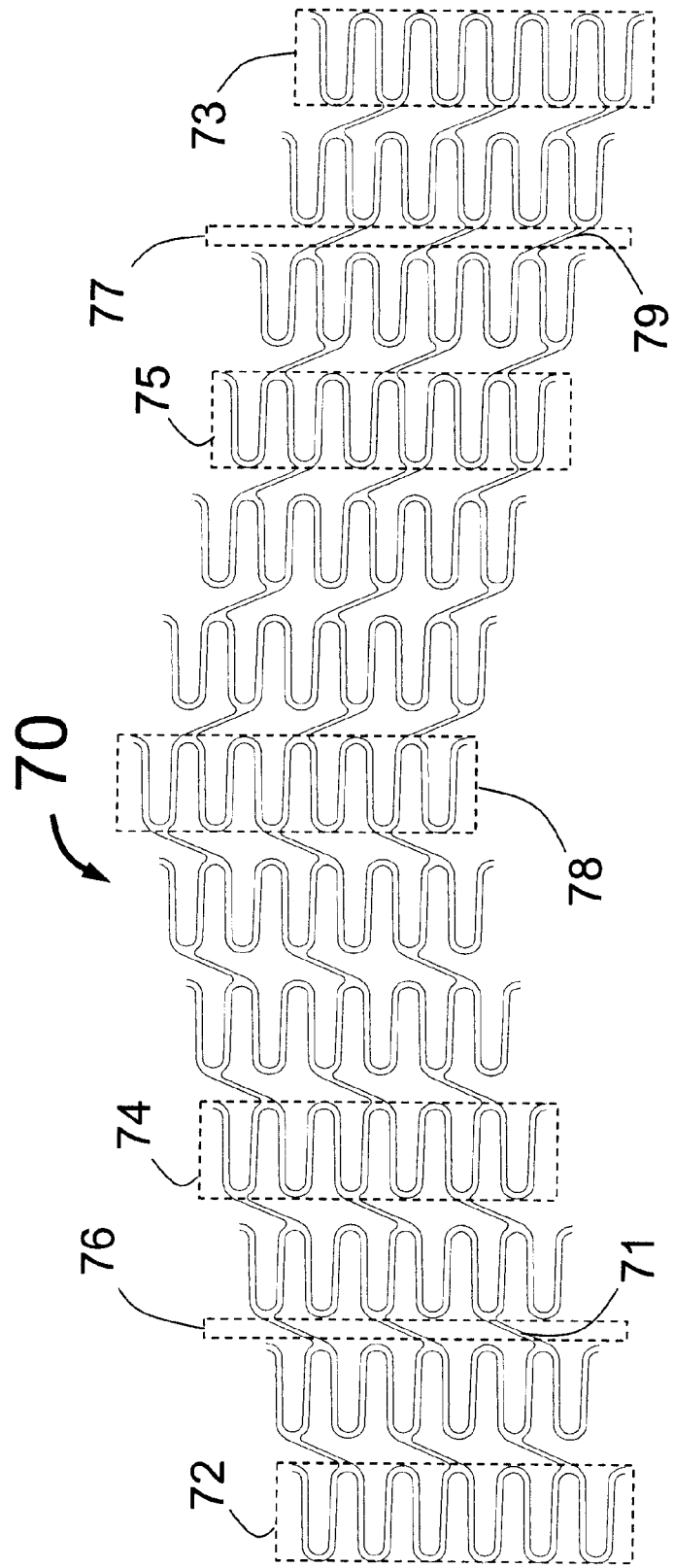
FIG. 7 is flat layout view of the present invention stent with tapered crowns and out-of-phase circumferential sets of strut members where the helical connectors in the left side (proximal portion) of the stent have an opposite slope as compared to the connectors on the right side (distal portion) of the stent.

FIG. 7 is flat layout view of a preferred embodiment of the present invention which is the stent 70 that has a proximal end (left side) circumferential set of strut members 72, a distal end (right side) circumferential set of strut members 73, proximal-central section circumferential sets of strut members 74, distal-central section circumferential sets of strut members 75 and a centered circumferential set of strut members 78. The proximal sets of helical connectors 76 have a positive slope and connect on both ends to the proximal-central section circumferential sets of strut members 74 or the centered circumferential set of strut members 78. The proximal sets of helical connectors 76 include individual connectors 71 each of which has a positive slope. Each individual helical connector 79 of each distal set of helical connectors 77 connect on each end to the distal-central section circumferential sets of strut members 75 or the centered circumferential set of strut members 78. The distal sets of helical connectors 77 include individual connectors 79 each of which has a negative slope. It is advantageous to have helical connector sets 76 and 77 slope in opposite directions so as to reduce the end-to-end stent twisting during expansion that does occur with the stent 10 of FIG. 2 that has all of the helical connectors having a positive slope. The optimum design for the stent 70 has one central circumferential set of strut members 78 so that the stent 70 has an equal number of helical connectors that have a positive slope and a negative slope. That is, the number of sets of helical connectors 76 with positive slopes is equal to the number of sets on helical connectors 77 that have negative slopes. Therefore, the optimum design of the stent 70 has a total number of circumferential sets of strut members which is an odd number and an equal number of circumferential sets of strut members 74 and 75.

Although the preferred embodiment of the stent 70 has an exactly equal number of helical connectors having positive and negative slopes, a small difference in the number of such connectors could still provide for a workable stent design. For example, there might be one more set of positive helical connectors 76 than sets of negative helical connectors 77 or there could be one more set of negative helical connectors 77 than sets of positive helical connectors 76. Furthermore, for very long stents, the stent might be a multiple of the design of FIG. 7 with, for example, four sections, the first and third having positive slope helical connectors 76 and the second and fourth having negative slope helical connectors 77. For such a stent, it is envisioned that every circumferential set of strut members is of the half-slot design which has greater flexibility and decreased fish scaling as compared to the use of circumferential sets of strut members that are the full slot design.

For each of the stent designs as taught herein, the circumferential extent of every straight helical connector has an arc length that is less than 90 degrees. Any angular extension that is much greater than even 60 degrees would result in additional twisting of the adjacent sets of circumferential strut members of the deployed stent which would be highly undesirable. In addition, helical connectors greater than 90 degrees may act as a restraint to balloon expansion of the stent. This is why pure helical stent designs are never used for balloon expandable stents even though they do work for self expanding stents such as those shown in the Burpee et al U.S. Pat. No. 7,556,644. It should also be noted that the tangential connection of the helical connectors allows those connectors to be truly arcs of a circle that have curvature in only one plane. This is in contradistinction to connectors that appear to be curved in their flat, layout view. This tangential connection design improves the stent's resistance to fracture during the fatigue bending testing that is required for approval for human use by regulatory bodies such as the US FDA. The tangential connection of the helical connectors to the outer curve of each of the connected curved crown of each circumferential set of strut members is a unique and valuable aspect of the design of the stents as described herein.

Stents are typically manufactured by laser cutting of a thin-walled tube followed by electropolishing to smooth all surfaces and edges. Current materials for stents include stainless steel, tantalum, cobalt chromium alloys such as L605 and special multi-layer composites structures. It should also be understood that the stents described herein could be bare metal or carbon or drug coated to reduce thrombus or carbon coated with elution of an anti-restenosis drug such as sirolimus or any other drug (such as everolimus) which can reduce restenosis. It is conceived that the stent 40 could be coated with a polymer from which an anti-restenosis drug such as sirolimus or everolimus could be eluted. If a polymer is used for eluting the anti-restenosis drug, a bioabsorbable polymer would be preferred over a polymer that would remain on the surface of the stent. The stent could also elute an anti-restenosis drug from pores created in the outer surface of the stent by etching or other means. An optimum design for the stent 40 would be to have a porous carbon coating that can elute sirolimus or everolimus without the use of any polymer. Such a stent would reduce both post-implant thrombosis and restenosis without any potential for irritating the artery wall that can occur if the stent has any polymer coating whether bioabsorbable or permanent.

Although the principal use of the present invention will be for implantation into coronary arteries, it should be understood that the stent described herein can be used in any vessel of the human body including by-pass vein grafts, peripheral veins and arteries and other vessels of the human body.

While the primary type of stent used in coronary arteries is a balloon expandable stent, many of the inventive design principles described herein can also be applied to self-expanding stent typically made of the shape memory metal Nitinol.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A balloon expandable stent in the form of a thin-walled, lace-like, cylindrical tubular structure having a multiplicity of circumferential sets of strut members, each circumferential sets of strut members comprising:

a series of alternating straight segments and arcuately contoured crowns defining an interior surface and an exterior surface;

each circumferential set of strut members being formed of an undulating array of individual strut elements, each of said strut elements having an arcuately contoured crown connected to a next succeeding strut element by a straight segment, alternating ones of each of the strut elements being connected to an adjacent circumferential set of strut members by a set of helical connectors that are connected to every other arcuately contoured crown of each of said strut members, each of the arcuately contoured crowns having a tapered width with the strut width at an apex of each crown being greater than the strut width at the ends of each crown defined by where the crown attaches to its adjacent straight segments, each crown having a arcuately contoured interior surface, the sets of helical connectors having slopes which are either positive or negative and the circumferential extent for each helical connector being less than 90 degrees, said interior surface of a crown connected to a helical connector defining a radius of curvature which is different than a radius of curvature of a corresponding interior surface of a crown which is not connected to a helical connector.

2. The stent of claim 1 where there is a central circumferential set of strut members which has a half slot length and that central circumferential set of strut members is joined on one side to helical connectors having a negative slope and on its opposite side it is joined to helical connectors having a positive slope.

3. The stent of claim 1 where the shape of each connected crown is different from the shape of each unconnected crown so that both connected and unconnected crowns have approximately the same material strain when the stent is expanded to its maximum rated diameter.

4. The stent of claim 1 where the straight portion of each helical connector is at least 30% smaller in width as compared to the average width of the unconnected crowns of the circumferential sets of strut members.

5. The stent of claim 1 where each helical connector has two parallel edges at least one of which is joined to an outer curve portion of a connected crown.

6. The stent of claim 1 where each adjacent circumferential set of strut members is out-of-phase with its adjacent circumferential set of strut members.

7. The stent of claim 1 where each adjacent circumferential set of strut members is in-phase with its adjacent circumferential set of strut members.

8. The stent of claim 1 where the length of the stent is less than 1.5 mm.

9. The stent of claim 1 where the length of the stent lies between 0.8 and 1.3 mm 10. The stent of claim 1 where the stent is coated with carbon to decrease the formation of thrombus.

11. The stent of claim 1 where the stent is coated with a porous carbon which contains an anti-restenosis drug that is eluted into the arterial wall after the stent is expanded into a coronary or peripheral artery.

12. The stent of claim 10 where a drug that is eluted is chosen from the group that includes sirolimus, everolimus or any analog of sirolimus.

13. The stent of claim 1 where the stent is coated with a polymer into which an anti-restenosis drug has been placed, the anti-restenosis drug being designed to elute into the arterial wall of an artery into which the stent has been first delivered and then expanded.

14. The stent of claim 13 where the polymer is bioabsorbable.

15. The stent of claim 1 where the number of sets of helical connectors that have a positive slope is equal to the number of sets of helical connectors that have a negative slope.

16. The stent of claim 1 said helical connectors have alternating positive and negative slopes.

17. A balloon expandable stent in the form of a thin-walled, lace-like, cylindrical tubular structure having a multiplicity of circumferential sets of strut members;

each circumferential set of strut members comprising a series of alternating straight segments and connected and unconnected arcuately contoured crowns where said connected arcuately contoured crowns are defined by a set of helical connections which are connected to the arcuately contoured crowns;

each circumferential set of strut members being connected to an adjacent circumferential set of strut members by a multiplicity of said helical connectors having connections to the outer curves of the connected arcuately contoured crowns of the adjacent circumferential sets of strut members;

where a radius of curvature of each connected crown is different from the radius of curvature of each unconnected crown so that both connected and unconnected crowns have approximately the same material strain when the stent is expanded to its maximum rated diameter.

18. The stent of claim 17 where the stent is coated with carbon to decrease the formation of thrombus.

19. The stent of claim 17 where the stent is coated with a porous carbon which contains an anti-restenosis drug that is eluted into the arterial wall after the stent is expanded into a coronary or peripheral artery.

20. The stent of claim 19 where the drug that is eluted is chosen from the group that includes sirolimus, everolimus or any analog of sirolimus.

21. The stent of claim 17 where the stent is coated with a polymer into which an anti-restenosis drug has been placed, the anti-restenosis drug being designed to elute into the arterial wall of an artery into which the stent has been first delivered and then expanded.

* * * * *